United States Patent
Nadanami et al.

(10) Patent No.: US 7,189,364 B2
(45) Date of Patent: Mar. 13, 2007

(54) HYDROGEN SENSOR

(75) Inventors: Norihiko Nadanami, Aichi (JP);
Tomonori Kondo, Aichi (JP); Masaya Watanabe, Aichi (JP); Ryuji Inoue, Gifu (JP); Noboru Ishida, Gifu (JP); Takafumi Oshima, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 668 days.

(21) Appl. No.: 10/119,901

(22) Filed: Apr. 11, 2002

(65) Prior Publication Data

US 2002/0187075 A1 Dec. 12, 2002

(30) Foreign Application Priority Data

Apr. 12, 2001 (JP) .............................. 2001-113610

(51) Int. Cl.
- B32B 5/02 (2006.01)
- B32B 27/04 (2006.01)
- B32B 27/12 (2006.01)
- G01N 27/00 (2006.01)
- G01N 7/00 (2006.01)

(52) U.S. Cl. .................... 422/98; 422/83; 422/90; 438/48; 438/49; 436/43; 436/144; 436/149; 73/1.01; 73/1.02; 73/23.2

(58) Field of Classification Search .................. 422/98, 422/83, 90; 438/48, 49; 436/43, 144, 149; 73/1.01, 1.02, 23.2

See application file for complete search history.

(56) References Cited

U.S. PATENT DOCUMENTS

| | | | |
|---|---|---|---|
| 5,322,602 A | | 6/1994 | Razaq |
| 5,573,648 A | * | 11/1996 | Shen et al. ................ 204/412 |
| 5,672,811 A | * | 9/1997 | Kato et al. .................. 73/31.05 |
| 5,935,398 A | * | 8/1999 | Taniguchi et al. .......... 204/424 |
| 6,073,478 A | | 6/2000 | Kuriakose et al. |
| 6,200,443 B1 | * | 3/2001 | Shen et al. ................ 204/401 |
| 6,517,693 B2 | * | 2/2003 | Taniguchi ................... 204/421 |
| 6,528,191 B1 | * | 3/2003 | Senner ........................ 429/12 |
| 6,652,723 B1 | * | 11/2003 | Nadanami et al. .......... 204/424 |

FOREIGN PATENT DOCUMENTS

| | | |
|---|---|---|
| EP | 1 037 041 A2 | 9/2000 |
| JP | 63-172952 | 7/1988 |
| JP | 1-287458 | 11/1989 |
| JP | 7-31153 | 4/1995 |

* cited by examiner

*Primary Examiner*—Brian Sines
(74) *Attorney, Agent, or Firm*—Sughrue Mion, PLLC

(57) ABSTRACT

A hydrogen sensor includes a first electrode 3 and a second electrode 4 provided in contact with a proton conduction layer 2; a gas diffusion controlling portion 6 provided between a measurement gas atmosphere and the first electrode 3; and a support element (1a, 1b) for supporting the proton conduction layer 6, the first electrode 3, the second electrode 4, and the gas diffusion controlling portion 6. Hydrogen contained in a measurement gas introduced via the gas diffusion controlling portion 6 is dissociated, decomposed, or reacted by applying a voltage between the first electrode 3 and the second electrode 4 to thereby generate protons. Hydrogen concentration is obtained on the basis of a limiting current generated as a result of the generated protons being pumped out via the proton conduction layer 2 from the first electrode 3 side of the proton conduction layer to the second electrode 4 side of the proton conduction layer. Hydrogen concentration on the first electrode 2 is controlled to a partial pressure of not less than $10^{-12}$ atm, or more preferably, of not less than $3\times10^{-12}$ atm and of less than $10^{-2}$ atm.

17 Claims, 4 Drawing Sheets

HYDROGEN SENSOR

BACKGROUND OF THE INVENTION

1. Field of the Invention

The present invention relates to a hydrogen sensor, and more particularly to a hydrogen sensor suited for measuring the concentration of hydrogen in a fuel gas, particularly a methanol-reformed gas, for use in a fuel

2. Description of Related Art

In response to concerns about global environmental pollution, in recent years extensive studies have been conducted on fuel cells for use as highly-efficient, clean power sources. Among such fuel cells, a polymer electrolyte fuel cell (PEFC) shows promise for various power sources including automobile use, by virtue of its advantages, such as operation at low temperature and high output density. A promising fuel gas for use in PEFC is a methanol-reformed gas or the like. In this connection, in order to enhance efficiency and like factors, a sensor capable of directly detecting hydrogen in a reformed gas is required.

Japanese Patent Publication (kokoku) No. 7-31153 proposes a sensor configured such that a working electrode, a counter electrode, and a reference electrode are disposed on an insulating base material while the three electrodes are unitarily covered with a gas permeable proton conductor membrane.

However, when the sensor disclosed in Japanese Patent Publication No. 7-31153 is used to measure the concentration of hydrogen in a methanol-reformed gas, unreacted methanol contained in the reformed gas influences the measurement of hydrogen concentration through the following mechanism: at a certain control electric potential set between the working electrode and the reference electrode (particularly when a high electric potential is set), methanol reacts with a resultant increase in current flowing between the working electrode and the counter electrode.

SUMMARY OF THE INVENTION

An object of the present invention is to provide a hydrogen sensor capable of accurately measuring the concentration of hydrogen in a measurement gas without being influenced by methanol contained in the measurement gas.

In order to achieve the above object, the present invention provides a hydrogen sensor comprising a proton conduction layer; a first electrode and a second electrode provided in contact with the proton conduction layer; a gas diffusion controlling portion provided between a measurement gas atmosphere and the first electrode; and a support element for supporting the proton conduction layer, the first electrode, the second electrode, and the gas diffusion controlling portion, wherein hydrogen contained in a measurement gas introduced via the gas diffusion controlling portion is dissociated, decomposed, or reacted through application of voltage between the first electrode and the second electrode to thereby generate protons, and hydrogen concentration is obtained on the basis of a limiting current generated as a result of the generated protons being pumped out via the proton conduction layer from the first electrode side of the proton conduction layer to the second electrode side of the proton conduction layer. The hydrogen sensor is characterized in that hydrogen concentration on the first electrode is controlled to a partial pressure of not less than $3 \times 10^{-12}$ atm, to thereby restrain reaction of methanol on the first electrode.

The present invention also provides a hydrogen sensor characterized in that a reference electrode is added to the above-described hydrogen sensor structure. In this hydrogen sensor, voltage applied between the first electrode and the second electrode can be varied such that electric potential between the first electrode and the reference electrode becomes constant, whereby an optimum voltage is applied between the first electrode and the second electrode at a certain hydrogen gas concentration or within a wide range of hydrogen gas concentration. Thus, a wider range of hydrogen concentration can be measured at higher accuracy. Even when resistance between the first electrode and the second electrode varies as a result of variation in the concentration of $H_2O$ in a measurement gas, the voltage applied between the first electrode and the second electrode can be controlled accordingly, and therefore hydrogen concentration can be measured at high accuracy even under great variation of measuring conditions related to hydrogen gas, $H_2O$, etc., contained in the measurement gas.

A preferred mode for carrying out the present invention will next be described.

According the preferred mode for carrying out the present invention, a first electrode and a second electrode are formed in opposition to each other with a proton conduction layer arranged therebetween. This configuration reduces resistance between the first and second electrodes, thereby enhancing the proton conduction capability of the proton conduction layer. Notably, when gas diffusion resistance of a diffusion controlling portion increases excessively, the sensitivity of a hydrogen gas sensor drops. Therefore, when sensitivity must be held at a certain appropriate level, the area of the first electrode and/or the second electrode is preferably increased. When sufficient sensitivity is attained, the first electrode and the second electrode can be formed on the same plane of the proton conduction layer.

The preferred mode for carrying out the present invention can use a polymer electrolyte, a glass material, a ceramic material, or a like material as a material for the proton conduction layer.

The preferred mode for carrying out the present invention uses a proton conduction layer which is formed of a polymer electrolyte and operates sufficiently at relatively low temperature; for example, not higher than 150° C., preferably not higher than 130° C., more preferably around 80° C., such as a proton conduction layer formed of a resin-type solid polymer electrolyte.

The preferred mode for carrying out the present invention uses one or more fluorine-containing resins as a material for the proton conduction layer, which proton conduction depends on humidity thereof. A specific example of the material is perfluorosulfonic acid membrane available as "NAFION" (registered trademark, product of DuPont), having a proton conduction or rather internal resistance which depends on relative humidity of the measurement gas (in other words it also depends on the temperature of the measurement gas).

In the preferred mode for carrying out the present invention, each electrode is a porous electrode which is made mainly of carbon or the like and carries a catalyst, such as Pt, on the side in contact with the proton conduction layer.

In the preferred mode for carrying out the present invention, each electrode is formed such that a layer containing a polymer electrolyte is formed on the side in contact with the proton conduction layer (interface between the electrode and the proton conduction layer) by applying a solution containing a polymer electrolyte similar to that of the proton conduction layer. As a result, the contact area between the proton conduction layer and a catalytic component carried by the electrode increases, thereby further enhancing proton conduction. Proton conduction can also be enhanced by reducing the thickness of the proton conduction layer.

According to the preferred mode for carrying out the present invention, the proton conduction layer, the electrodes, and a gas diffusion controlling portion are supported by a support element to thereby configure a unitary hydrogen gas sensor. The support element is formed of an inorganic insulator, such as alumina ceramic, or an organic insulator made of resin or a like material. The gas diffusion controlling portion is preferably formed of a gas permeable, porous alumina ceramic or a like material or may be configured such that one or more bores having a small cross-sectional area; for example, one or more through-holes each having a very small diameter, are formed in a portion of the support element formed of a dense material. Such a fine through-hole can be formed by use of, for example, a laser beam machining process or an ultrasonic machining process. When a laser beam machining process is used, the diameter of an opening may be adjusted by controlling the diameter of a laser beam, laser output, laser beam emission time, or a like condition. The average pore diameter of the above-mentioned porous material or the diameter of a through-hole(s) is preferably not less than 1 µm, whereby gas diffusion proceeds outside the region of Knudsen diffusion and thus pressure dependence can be reduced.

A hydrogen gas sensor according to the present invention is favorably used for measuring the concentration of hydrogen in a measurement gas atmosphere that contains methanol, particularly for measuring the concentration of hydrogen in a fuel gas, particularly a methanol-reformed gas containing $H_2O$, for use in a fuel cell.

Figure 1:
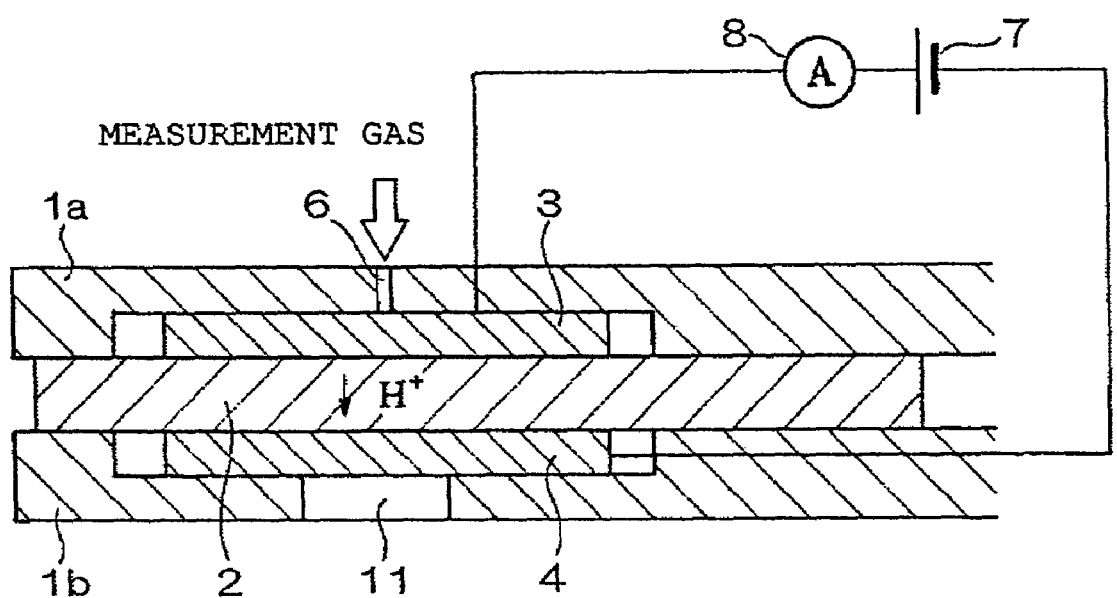
FIG. 1 is a sectional view illustrating the structure of a hydrogen sensor according to a first embodiment of the present invention.

Reference numerals are used to identify items shown in the drawings as follows:

1a, 1b: upper and lower support elements (substrates)
2: proton conduction layer
3: first electrode
4: second electrode
5: reference electrode
6: gas diffusion controlling portion (gas diffusion controlling aperture)
7: power supply
8: ammeter
9: variable power supply
10: electrometer (potentiometer)
11: hole (outlet)

DESCRIPTION OF THE PREFERRED EMBODIMENTS

Embodiments of the present invention will now be described, by way of example only, with reference to the accompanying drawings, in which:

Embodiment 1

FIG. 1 is a sectional view for explaining a hydrogen sensor according to a first embodiment of the present invention. Referring to FIG. 1, this hydrogen sensor is configured such that a first electrode 3 and a second electrode 4 are formed in opposition to each other with a proton conduction layer 2 arranged therebetween. The first electrode 3 and the second electrode 4 are in contact with the proton conduction layer 2. The first electrode 3, the proton conduction layer 2, and the second electrode 4 are held between an upper support element 1a and a lower support element 1b, which constitute a support element. A gas diffusioncontrolling portion 6 for introducing a measurement gas onto the first electrode 3 is formed in the upper support element 1a. A hole 11 for draining out hydrogen recombined at the second electrode 4 is formed in the lower support element 1b, in contact with the second electrode 4. A power supply 7 and an ammeter 8 are connected between the first electrode 3 and the second electrode 4 via lead portions, thereby enabling application of voltage and measurement of current.

The proton conduction layer 2 is formed of a fluorine-containing resin which operates at relatively low temperature of –30 to 150° C.; for a preferable example, NAFION (trademark, product of DuPont). Each of the first electrode 3 and the second electrode 4 is a porous electrode which is made of carbon or the like and carries a catalyst, such as Pt, on the side in contact with the proton conduction layer 2. The insulating support element (the upper support element 1a and the lower support element 1b) is formed of a ceramic such as alumina. Notably, the support element can also be formed of a resin or a like material. The gas diffusion-controlling portion 6 may be formed of porous alumina. Notably, the gas diffusion controlling portion 6 is formed of very fine holes. Alternatively, the gas diffusion controlling portion 6 may assume the form of a small hole or aperture having a diameter of about 0.5 mm or may be a porous member so that the gas diffusing onto the first electrode 3 is controlled or limited. The proton conduction layer 2, the first electrode 3, and the second electrode 4 are physically held in the support member, in contact with one another. Notably and preferably, the proton conduction layer 2, the first electrode 3, and the second electrode 4 may be bonded together using a hot pressing process.

Next, the principle of measuring hydrogen concentration by use of the above-described hydrogen sensor will be described with reference to FIG. 1.

(1) Hydrogen which has entered through the gas diffusion controlling portion 6 and reacted on the first electrode 3 is dissociated into protons by the catalytic action of Pt or a like catalyst contained in the first electrode 3 and under a voltage applied across the first electrode 3 and the second electrode 4, thereby generating protons.

(2) The generated protons are pumped out toward the second electrode 4 through the proton conduction layer 2 and become hydrogen gas again. The hydrogen gas diffuses out or rather drains out into the measurement gas atmosphere via the hole 11 that has a larger opening than that of the diffusion controlling portion 6.

Figure 2:
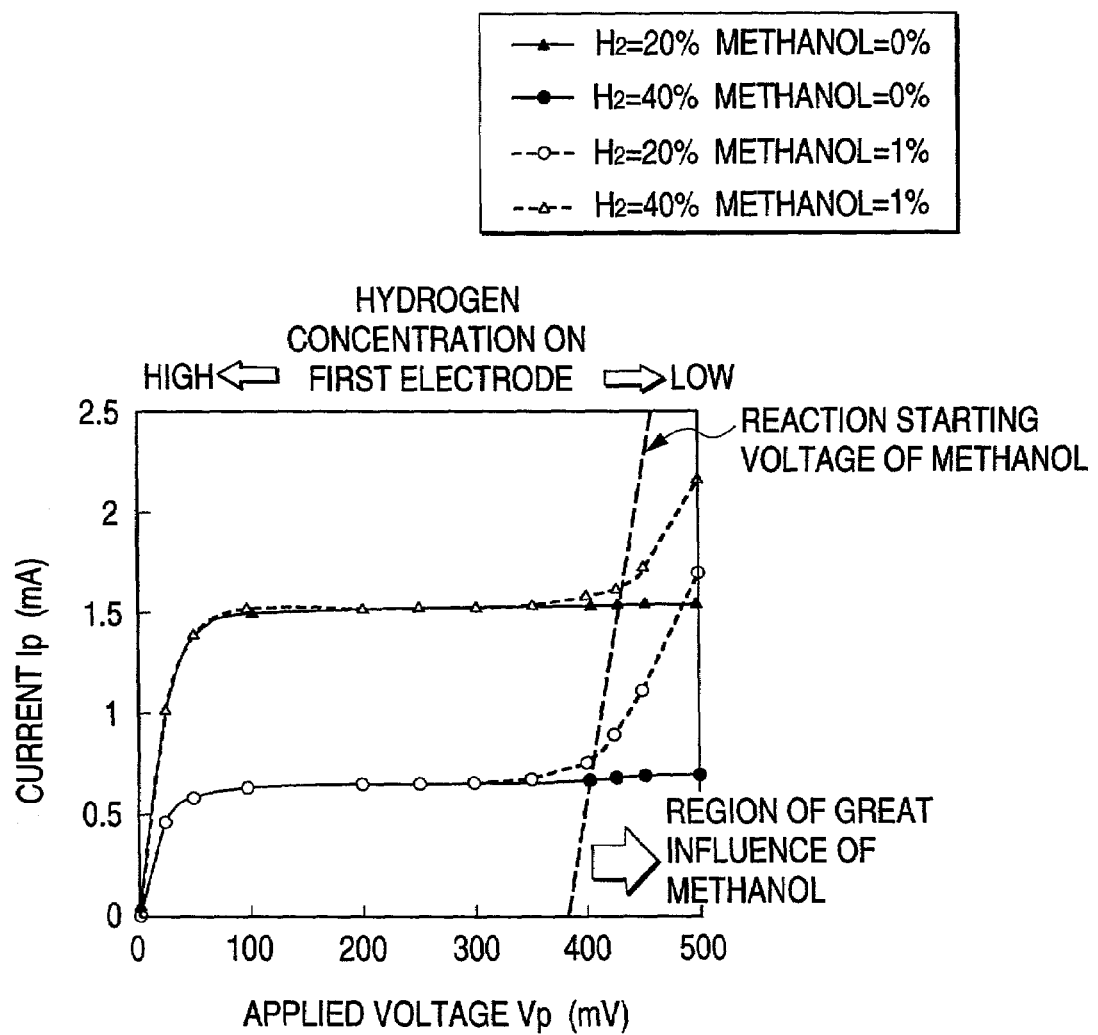
FIG. 2 is a graph for explaining the results of Measurement Example 1.

(3) At this time, current flowing between the first electrode 3 and the second electrode 4 appears flat or constant in a certain voltage range as shown in FIG. 2. This flat current is called a limiting current which becomes proportional to the concentration of hydrogen in a measurement gas when the applied voltage is sufficiently high or approximately more than 50 mV (corresponding to about $10^{-2}$ atm of hydrogen partial pressure). This limiting current is achieved because the gas amount entering onto the electrode 3 is limited by the diffusion-controlling portion 6. If the applied voltage is too high or approximately more than 425 mV, gas such as methanol other than hydrogen starts to dissociate thereby increasing the current drastically so as not proportionally representing the hydrogen concentration of the measurement gas. In this way, on the basis of the flat current (limiting current), the concentration of hydrogen contained in the measurement gas is obtained.

MEASUREMENT EXAMPLE 1

The concentration of hydrogen in a measurement gas was measured using a hydrogen sensor according to the above-described first embodiment while the measuring conditions were varied, whereby the difference in voltage-current characteristics between the presence and absence of methanol was studied. Specifically, current flowing between the first electrode and the second electrode was measured with respect to various measurement gas compositions while the voltage applied between the first electrode and the second electrode was varied. The measuring conditions are itemized below.

Measuring Conditions
    Measurement gas composition: 20% or 40% $H_2$, 15% $CO_2$, 25% $H_2O$, 0% or 1% $CH_3OH$, $N_2$ as balance
    Measurement gas temperature: 80° C.
    Measurement gas flow rate: 10 L/min
    Voltage Vp applied between first and second electrodes: 0–500 mV FIG. 2 is a graph for explaining the results of Measurement Example 1. As is apparent from FIG. 2, a limiting current is formed at an applied voltage Vp of about 50 mV or higher but of less than about 425 mV. The magnitude of this limiting current varies in proportion to hydrogen concentration, indicating that the hydrogen concentration can be measured based on the flat limiting current by use of the hydrogen sensor according to the first embodiment.

As shown in FIG. 2, when methanol is present in a measurement gas, the magnitude of current (Ip: current flowing between the first electrode and the second electrode) begins to increase with voltage at a Vp of about 400 mV or more. The relationship between applied voltage Vp and current Ip can be expressed by Eq. 1 given below.

$$Vp = Ip \times r + EMF \quad \text{[Eq. 1]}$$

where
    Vp: Voltage applied between first electrode and second electrode
    Ip: Current flowing between first electrode and second electrode
    r: Resistance between first electrode and second electrode
    EMF: Electromotive force generated between first electrode and second electrode according to Nernst equation ([Eq. 2]).

$$EMF = RT/2F \times Ln(P_2/P_1) \quad \text{[Eq. 2]}$$

where
    R: Gas constant (8.314 J/mol·K)
    T: Absolute temperature (K)
    F: Faraday constant (9.649×10⁴ C/mol)
    $P_1$: Partial pressure of hydrogen on first electrode (atm)
    $P_2$: Partial pressure of hydrogen on second electrode (atm)

Values appearing in Table 1 shown below were substituted into Eq. 1 and Eq. 2 described above to thereby obtain the partial pressure $P_1$ of hydrogen on the first electrode at which $P_1$ the influence of methanol begins to emerge, with respect to an $H_2$ concentration of 20% and 40%. $P_1$ was $2.1 \times 10^{-12}$ atm at an $H_2$ concentration of 20%; and $P_1$ was $3.0 \times 10^{-12}$ atm at an $H_2$ concentration of 40%. These results reveal that, when hydrogen partial pressure on the first electrode is lower than $3 \times 10^{-12}$ atm, the influence of methanol contained in the measurement gas on measurement of hydrogen concentration increases enormously. Therefore, by controlling the partial pressure of hydrogen on the first electrode to not less than $3 \times 10^{-12}$ atm, even when methanol is present, hydrogen concentration of the measurement gas can be measured without being greatly influenced by methanol.

TABLE 1

| | | |
|---|---|---|
| Concentration of hydrogen in measurement gas (%) | 20 | 40 |
| Reaction starting voltage of methanol contained in measurement gas Vp (mV) <from FIG. 2> | 400 | 425 |
| Limiting current Ip (mA) <from FIG. 2> | 0.662 | 1.531 |
| Resistance between first and second electrodes r (Ω) | 23.3 | |
| Measurement gas temperature (° C.) | 80 | |
| Partial pressure of hydrogen on second electrode (atm) | 0.2 | 0.4 |
| Partial pressure of hydrogen on first electrode at which influence of methanol contained in measurement gas begins to emerge (atm) | $2.1 \times 10^{-12}$ | $3.0 \times 10^{-12}$ |

Embodiment 2

Next, a hydrogen sensor according to a second embodiment of the present invention will be described. The structure of the hydrogen sensor according to the second embodiment differs from that of the hydrogen sensor according to the first embodiment in that a reference electrode is added. The following description of the second embodiment mainly covers the difference of the second embodiment from the first embodiment. For structural features of the hydrogen sensor according to the second embodiment similar to those of the hydrogen sensor according to the first embodiment, the description of the first embodiment may be referred to as appropriate.

Figure 3:
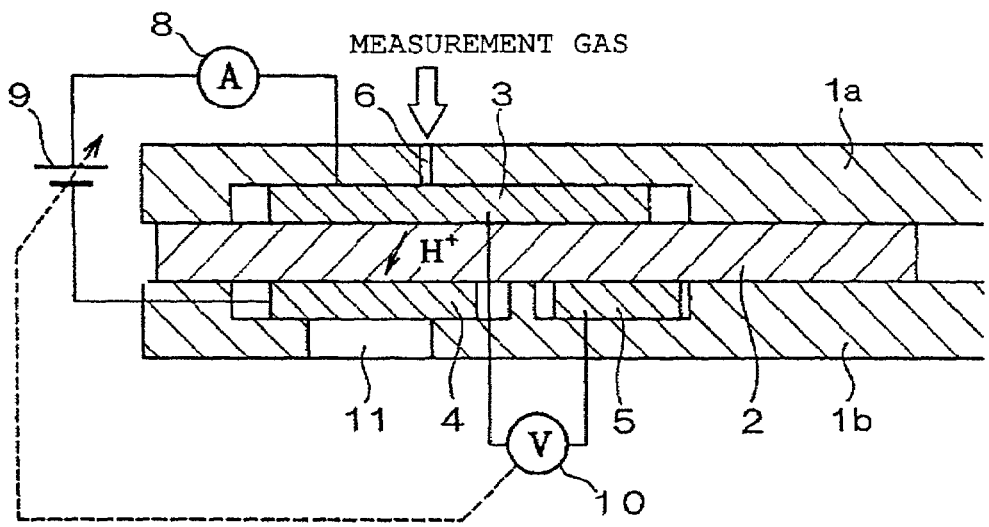
FIG. 3 is a sectional view illustrating the structure of a hydrogen sensor according to a second embodiment of the present invention.

FIG. 3 is a sectional view illustrating the structure of the hydrogen sensor according to the second embodiment of the present invention. Referring to FIG. 3, this hydrogen sensor is configured such that a reference electrode 5 is formed in contact with the proton conduction layer 2. The reference electrode 5 is so formed that the hydrogen concentration in the vicinity of the reference electrode 5 is not affected by variation of the concentration of hydrogen in a measurement gas. The reference electrode 5 and the second electrode 4 are formed on the same surface of the proton conduction layer 2 and disposed in different chambers.

In order to further stabilize hydrogen concentration on the reference electrode 5 (so as not to be affected by the hydrogen concentration variation of the measurement gas), the reference electrode 5 is preferably a self-generation-type reference electrode. This can be attained in the following manner: a constant very small current is caused to flow from the first electrode 3 to the reference electrode 5 such that a portion of the hydrogen leaks to the exterior of the sensor via a predetermined leakage resistance portion (e.g., a very fine hole).

An electrometer 10 is connected between the first electrode 3 and the reference electrode 5 via lead portions. A variable power supply 9 and the ammeter 8 are connected between the first electrode 3 and the second electrode 4 via lead portions. Sufficient voltage is applied between the first electrode 3 and the second electrode 4 such that the electric potential between the first electrode 3 and the reference electrode 5 assumes a constant value. At this time, current flowing between the first electrode 3 and the second electrode 2 is measured.

Next, the principle of measuring hydrogen concentration by use of the above-described hydrogen sensor will be described with reference to FIG. 3.

(1) Hydrogen gas which has reached the first electrode 3 through the gas diffusion controlling portion 6 generates an electromotive force, according to its concentration, between the first electrode 3 and the reference electrode 5 via the proton conduction layer 2.

(2) Voltage is applied between the first electrode 3 and the second electrode 4 such that the hydrogen concentration on the first electrode 3 becomes constant; i.e., the electric potential between the first electrode 3 and the reference electrode 5 becomes constant.

(3) As a result, hydrogen is dissociated into protons on the first electrode 3. The thus-generated protons are pumped out toward the second electrode 4 through the proton conduction layer 2 to regenerate hydrogen gas. The hydrogen gas diffuses into the measurement gas atmosphere.

(4) At this time, a limiting current flowing between the first electrode 3 and the second electrode 4 is proportional to the concentration of hydrogen in a measurement gas. Therefore, on the basis of the current, the concentration of hydrogen in the measurement gas can be obtained.

The hydrogen sensor according to the second embodiment of the present invention can control hydrogen concentration on the first electrode to a constant level while voltage applied between the first electrode and the second electrode is optimally varied according to the concentration of hydrogen in a measurement gas (i.e., high voltage is applied at high concentration, and low voltage is applied at low concentration) such that the electric potential between the first electrode and the reference electrode becomes constant.

Even when resistance between the first electrode and the second electrode increases because of variation in, for example, the concentration of $H_2O$ in a measurement gas, the hydrogen sensor according to the second embodiment of the present invention can control hydrogen concentration on the first electrode to a constant level by varying the applied voltage as appropriate. Thus, by setting the electric potential between the first electrode and the reference electrode to the optimum value, this hydrogen sensor can always control hydrogen concentration on the first electrode to a partial pressure of not less than $3 \times 10^{-12}$ atm even when used in an atmosphere whose hydrogen concentration, $H_2O$ concentration, etc., vary greatly. Therefore, even when methanol is present under a varying condition, hydrogen concentration can be accurately measured over a wide concentration range without being influenced by methanol.

Measurement Example 2

By use of the hydrogen sensor according to the second embodiment, the dependence of current flowing between the first electrode and the second electrode on methanol contained in a measurement gas was studied while electric potential Vs (i.e., reading of the potentiometer 10) set between the first electrode and the reference electrode was varied. In this measurement, in order to stabilize hydrogen concentration on the reference electrode, a constant very small current is caused to flow from the first electrode to the reference electrode such that the reference electrode functions as a self-generation-type reference electrode. Measuring conditions are itemized below.

Figure 4:
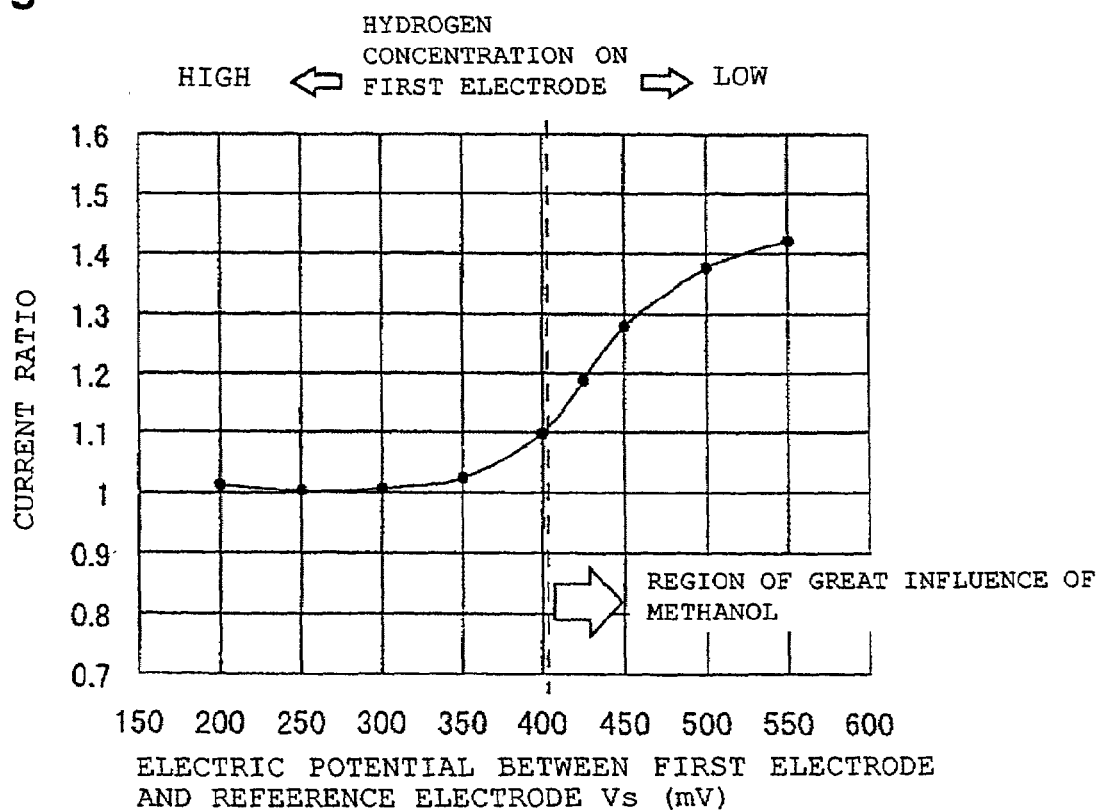
FIG. 4 is a graph for explaining the results of Measurement Example 2.

Measuring Conditions
    Measurement gas composition: 40% $H_2$, 15% $CO_2$, 25% $H_2O$, 0% or 1% $CH_3OH$, $N_2$ as balance
    Measurement gas temperature: 80° C.
    Measurement gas flow rate: 10 L/min
    Electric potential Vs between first electrode and reference electrode: 200–550 mV
    Very small current caused to flow for establishing self-generation-type reference electrode: 10 μA FIG. 4 is a graph for explaining the results of Measurement Example 2. In FIG. 4, current flowing between the first electrode and the second electrode; i.e., the dependence of measured hydrogen concentration on methanol, is represented by the ratio between current at a methanol concentration of 0% and current at a methanol concentration of 1%; i.e., current at a methanol concentration of 1%/current at a methanol concentration of 0%. Thus, a current ratio closer to 1 indicates lower dependence on methanol.

As is apparent from FIG. 4, when electric potential Vs between the first electrode and the reference electrode is greater than 400 mV, the current ratio is 1.1 or greater, indicating greater dependence on methanol. Therefore, by setting the Vs value to not greater than 400 mV to thereby control hydrogen concentration on the first electrode to a level at which methanol does not react, even when methanol is present, hydrogen gas concentration can be accurately measured without being influenced by methanol.

Embodiments 3 and 4

Figure 5:
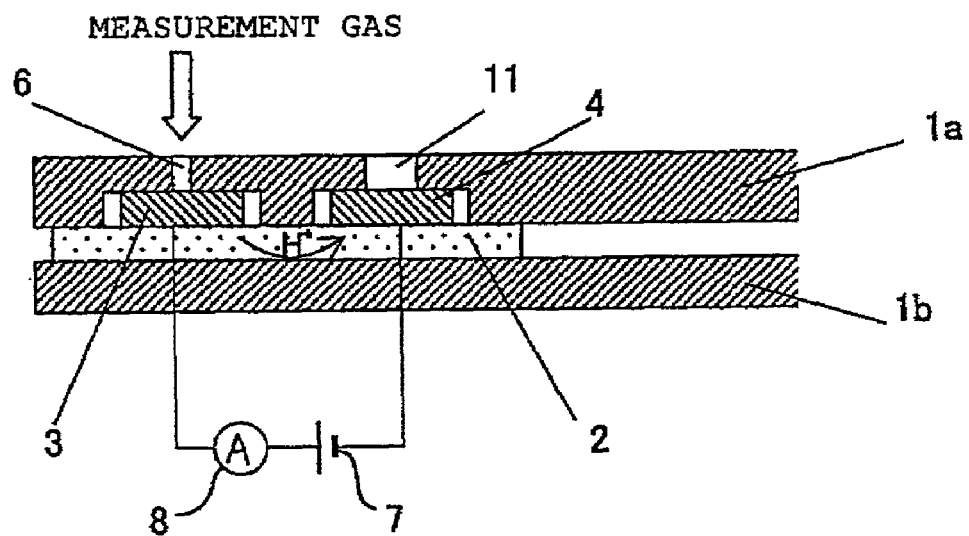
FIG. 5 is a sectional view illustrating the structure of a hydrogen sensor according to a third embodiment of the present invention.
Figure 6:
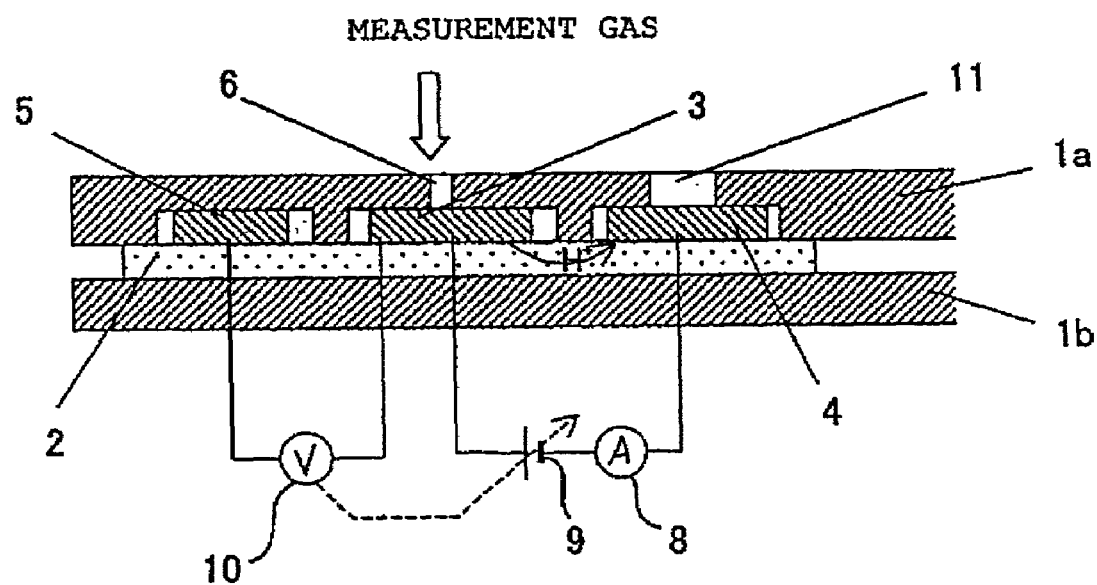
FIG. 6 is a sectional view illustrating the structure of a hydrogen sensor according to a fourth embodiment of the present invention.

FIG. 5 and FIG. 6 respectively show hydrogen sensors according to third and fourth embodiments according to the invention, wherein the first electrode 3, the second electrode 4 and/or the reference electrode 5 are formed on the same surface of the proton conduction layer 2 and in different chambers respectively defined and sealed by upper support element 1a and the proton conduction layer 2. The other surface of the proton conduction layer 2 is pushed and supported by a lower supporting element 1b. A gas diffusion portion (small aperture) 6 is formed penetrating in the upper support element so as to introduce a measurement gas containing hydrogen onto the first electrode 3. A drain hole (outlet) 11 for draining out hydrogen recombined at the second electrode 4 from the chamber in which the second electrode is sealed in is formed penetrating through the upper supporting element 1a. The basic function of the hydrogen sensor according to the third embodiment (as shown in FIG. 5) is similar to that of the first embodiment as shown in FIG. 1, and the basic function of the hydrogen sensor according to the fourth embodiment (as shown in FIG. 6) is similar to that of the second embodiment as shown in FIG. 3.

Effect of the Invention

The hydrogen sensor of the present invention can accurately measure hydrogen concentration without being influenced by methanol contained in a measurement gas. Therefore, the hydrogen sensor of the present invention can accurately measure the concentration of hydrogen in a fuel gas for use in a fuel cell, particularly the concentration of hydrogen in a methanol-reformed gas without being influenced by methanol.

It should further be apparent to those skilled in the art that various changes in form and detail of the invention as shown and described above may be made. It is intended that such changes be included within the spirit and scope of the claims appended hereto.

This application is based on Japanese Patent Application No. 2001-113610 filed Apr. 12, 2001, the disclosure of which is incorporated herein by reference in its entirety.

What is claimed is:

1. A hydrogen sensor comprising:
 a proton conduction layer;
 a first electrode and a second electrode provided in contact with the proton conduction layer;
 a gas diffusion controlling portion provided between a measurement gas containing hydrogen and the first electrode; and
 a support element for supporting the proton conduction layer, the first electrode, the second electrode, and the gas diffusion controlling portion;
 means for controlling hydrogen concentration on the first electrode to a partial pressure of not less than $3 \times 10^{-12}$; and
 voltage control means for controlling the voltage applied across the first and second electrodes to not be greater than 425 mV,
 wherein hydrogen introduced via the gas diffusion controlling portion is dissociated, decomposed or reacted by applying a voltage between the first electrode and the second electrode to thereby generate protons, said protons being pumped via the proton conduction layer from a first electrode side of the proton conduction layer to a second electrode side of the proton conduction layer to generate a limiting current, and the hydrogen concentration of the measurement gas is determined based on said limiting current.

2. The hydrogen sensor as claimed in claim 1, wherein hydrogen concentration on the first electrode is controlled by means of the voltage applied between the first electrode and the second electrode.

3. The hydrogen sensor as claimed in claim 1, adapted to measure the concentration of hydrogen in a measurement gas atmosphere which contains methanol.

4. The hydrogen sensor as claimed in claim 1, adapted to measure the concentration of hydrogen in a fuel gas for use in a fuel cell.

5. A hydrogen sensor comprising:
 a proton pump comprising a proton conduction layer and first and second electrodes contacting the proton conduction layer;
 a gas diffusion controlling portion provided between a measurement gas containing hydrogen and the first electrode;
 a support for supporting the proton conduction layer, the first electrode, the second electrode, and the gas diffusion controlling portion;
 means for applying a voltage between the first and second electrodes so as to dissociate, decompose or react hydrogen gas contacting the first electrode via the gas diffusion controlling portion to thereby generate protons, said proton pump pumping protons generated on the first electrode via the proton conduction layer to the second electrode so as to establish a limiting current;
 means for controlling hydrogen concentration on the first electrode to a partial pressure of not less than $3 \times 10^{-12}$ atm;
 voltage control means for controlling the voltage applied across the first an second electrodes to not be greater than 425 mV; and
 means for determining hydrogen concentration of the measurement gas based on said limiting current.

6. The hydrogen sensor as claimed in claim 5, wherein said proton conduction layer is arranged between said first and second electrodes.

7. The hydrogen sensor as claimed in claim 5, comprising an outlet in contact with the second electrode for releasing hydrogen generated by recombination of protons at the second electrode.

8. The hydrogen sensor as claimed in claim 5, wherein said support comprises first and second chambers housing said first and second electrodes, respectively, and the proton conduction layer is arranged between said first and second electrodes.

9. The hydrogen sensor as claimed in claim 5, wherein said first and second electrodes are disposed on a same side of the proton conduction layer.

10. The hydrogen sensor as claimed in claim 1, wherein the hydrogen sensor operates at a temperature of not higher than 150° C.

11. The hydrogen sensor as claimed in claim 1, wherein the proton conduction layer is made of a fluorine-containing resin.

12. The hydrogen sensor as claimed in claim 1, wherein said sensor detects hydrogen concentration in a measurement gas containing methanol and/or $H_2O$.

13. The hydrogen sensor as claimed in claimed in claim 1, further comprising a reference electrode provided in contact with the proton conduction layer, and said support element supporting the proton conduction layer, the first electrode, the second electrode, the reference electrode and the gas diffusion controlling portion,
 wherein the voltage applied between the first electrode and the second electrode establishes a constant electric potential between the first electrode and the reference electrode.

14. The hydrogen sensor as claimed in claim 13, wherein the electric potential between the first electrode and the reference electrode is not greater than 400 mV.

15. The hydrogen sensor as claimed in claim 5, further comprising a reference electrode contacting the proton conduction layer, and said support supporting the proton conduction layer, the first electrode, the second electrode, the reference electrode and the gas diffusion controlling portion,
 wherein the voltage applied between the first electrode and second electrode establishes a constant electric potential between the first electrode and the reference electrode.

16. The hydrogen sensor as claimed in claim 15, wherein said support comprises first, second and third chambers housing said first, second and reference electrodes, respectively, the proton conduction layer is arranged between the first and second electrodes, and the second electrode and the reference electrode are disposed on a same side of the proton conduction layer.

17. The hydrogen sensor as claimed in claim 1, capable of accurately measuring hydrogen concentration without being influenced by methanol contained in a measurement gas.

* * * * *